US005497786A

United States Patent [19]

Urick

[11] Patent Number: 5,497,786
[45] Date of Patent: Mar. 12, 1996

[54] APPARATUS AND METHOD FOR FORMABLE GUIDE WIRE TIP

[75] Inventor: Michael J. Urick, Rogers, Minn.

[73] Assignee: SCIMED Life Systems, Inc., Maple Grove, Minn.

[21] Appl. No.: 292,533

[22] Filed: Aug. 18, 1994

[51] Int. Cl.⁶ ..................................................... A61B 5/00
[52] U.S. Cl. ........................................ 128/772; 128/657
[58] Field of Search .................................... 128/657, 772; 604/164, 170, 280, 282

[56] References Cited

U.S. PATENT DOCUMENTS

| | | | |
|---|---|---|---|
| 4,554,929 | 11/1985 | Samson et al. | 128/772 |
| 4,682,607 | 7/1987 | Vaillancourt et al. | 128/772 |
| 4,832,097 | 5/1989 | Sepetka et al. | 128/772 |
| 4,846,186 | 7/1989 | Box et al. | 128/657 |
| 4,854,330 | 8/1989 | Evans et al. | 128/772 |
| 4,951,686 | 8/1990 | Herlitze | 128/772 |
| 4,971,490 | 11/1990 | Hawkins | 128/772 |
| 5,069,226 | 12/1991 | Yamauchi et al. | 128/772 |
| 5,084,022 | 1/1992 | Claude | 128/772 X |
| 5,112,136 | 6/1992 | Guglielmi et al. | 128/772 X |

Primary Examiner—Sam Rimell
Attorney, Agent, or Firm—Peter J. Gafner

[57] ABSTRACT

An apparatus and method for a catheter guide wire having a helical coil encasing or covering at least a portion of the distal end section of the wire. At least one region of the distal end is heat treated to facilitate bending or forming a J-tip. The treated regions are of a size to cover only a small portion of the distal end section of the wire, thus preserving the resilience and flexibility of the tip for steerage through a lumen of a body. This improved method and device enables the bending or forming of the guide wire tip with comparative ease with regard to non-treated tips, without sacrificing tip performance as often occurs when the entire or major portion of the distal tip is heat treated, or bent without treatment simply by force.

9 Claims, 6 Drawing Sheets

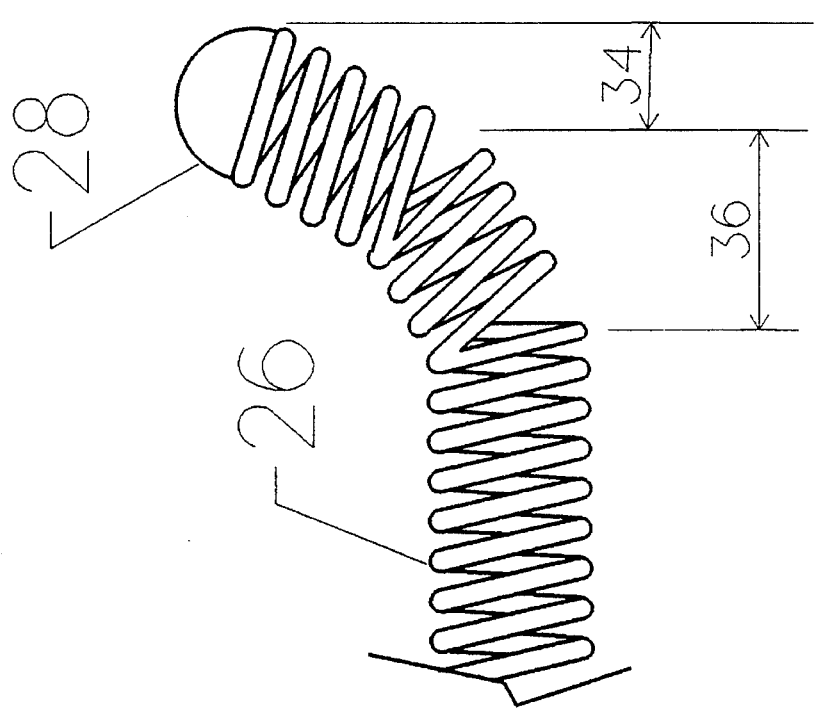

APPARATUS AND METHOD FOR FORMABLE GUIDE WIRE TIP

BACKGROUND OF THE INVENTION

1. Field of the Invention

The present invention relates in general to medical instrumentation, and more particularly to intraluminal devices, and still more particularly to guide wires for intraluminal catheters.

2. Description of the Prior Art

The use of intraluminal catheters for treatment of various medical problems within the body is well known. It is also well known that a variety of problems are encountered as the catheter is steered through the selected lumen to a desired point in the body. The path may be tortuous and the point of interest may be difficult to locate precisely. A continuing series of technical improvements and additions have been made in the catheter field to provide devices and methods which can overcome certain of the difficulties. One such series of improvements has resulted in the now well known use of a thin flexible guide wire which can be more easily steered through the lumen to the desired site. A selected catheter, such as a balloon catheter, can then be slid over the guide wire to reach the desired situs in the body.

It is now well known that providing a bend or "J-tip" to the distal end of the guide wire increases maneuverability of the guide wire through the lumen. Such J-tips are often set by the manufacturer of the guide wire, but it is also sometimes advantageous to have the physician or other operator create or modify the bend during an angioplasty procedure.

Certain disadvantages exist in this known prior art. For example, the material most commonly used for guide wires is stainless steel, for example, 304V stainless steel. The formation of a bend or J-tip at the distal end of such a metal wire requires a force which may be inconsistent or irregular thus significantly effecting the strength of the guide wire tip. One way to attempt to increase formability of the guide wire distal end may be to heat the tip. In the present art, the tip is often heated prior to cold working, in the case of stainless steel 304V to a temperature within the range of 700° to 1000° F. This procedure of increasing temperature followed by cold working of the stainless steel results in a less than optimum performance. It is also likely that heating the entire distal portion of the guide wire to the annealing temperature, approximately 1400° F. in the case of stainless steel 304V, may add too much formability to the wire tip, thus negatively effecting its tip strength and steering properties as it is guided through a body lumen.

As a general example of formable tip references in the prior art, see by way of example, U.S. Pat. No. 4,846,186, issued Jul. 11, 1989 to Box, et al; and U.S. Pat. No. 4,838,879, issued Jun. 13, 1989 to Tanabe, et al.

SUMMARY OF THE INVENTION

The present invention overcomes the described disadvantages of the prior art by providing an apparatus and method for a catheter guide wire having one or more distinct regions at its distal end, which regions are heat treated to provide the desired properties of a formable material, and which regions are sufficiently limited so as not to substantially reduce the flexibility and resilience of the rest of the guide wire distal end. Thus the J-tip formation may be easily and consistently achieved without compromising the guide wire tip performance.

BRIEF DESCRIPTION OF THE DRAWINGS

The objects and many of the attendant advantages of the present invention will be readily appreciated as it becomes better understood by reference to the following detailed description when considered in connection with the accompanying drawings, in which like reference numerals designate like parts throughout the figures thereof and wherein:

FIG. 6 is a view of a helical coil positioned as if attached to the distal end of the guide wire in FIG. 5 after multiple bending.

DETAILED DESCRIPTION OF THE PREFERRED EMBODIMENTS

Figure 1:
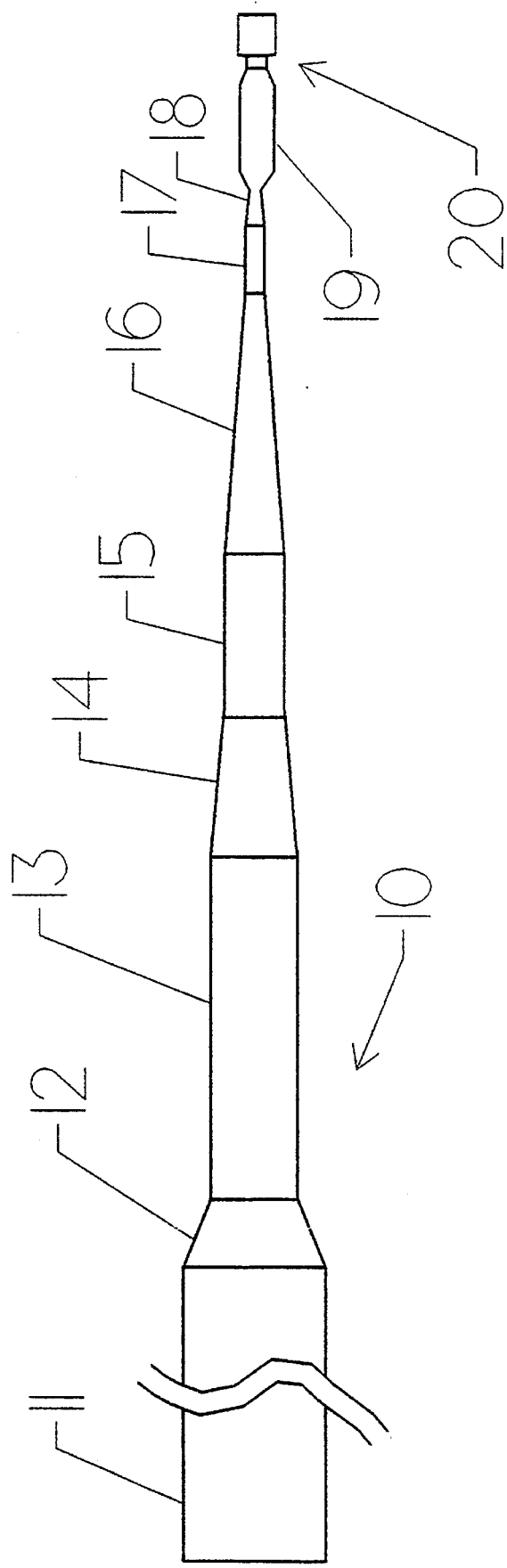
FIG. 1 is a plan view showing a prior art catheter guide wire.

FIG. 1 discloses a partial plan view of a catheter guide wire 10. Guide wire 10 is known in the prior art and is shown here as a preferred embodiment for the addition of the present invention. In addition to a proximal end 11, shown here in part, guide wire 10 includes a distal end comprising a plurality of alternating steps of continuous and tapering diameters shown here as tapering steps 12, 14, 16 and 18 alternating with continuous steps 13, 15 and 17. The distal ends include a distal tip section 19 connected between step 18 and a tip connection member shown generally as 20. In this preferred embodiment distal tip section 19 is shown as a flattened ribbon and will be referred to hereafter as ribbon 19.

Guide wire 10 of FIG. 1 is preferably constructed of a metal that contains a high degree of resiliency. Though there are several such materials with a higher degree of resiliency than stainless steel, in this particular embodiment stainless steel 304V has been selected as the preferred metal. Stainless steel 304V is known to have an annealing point at approximately 1400° F.

Figure 2:
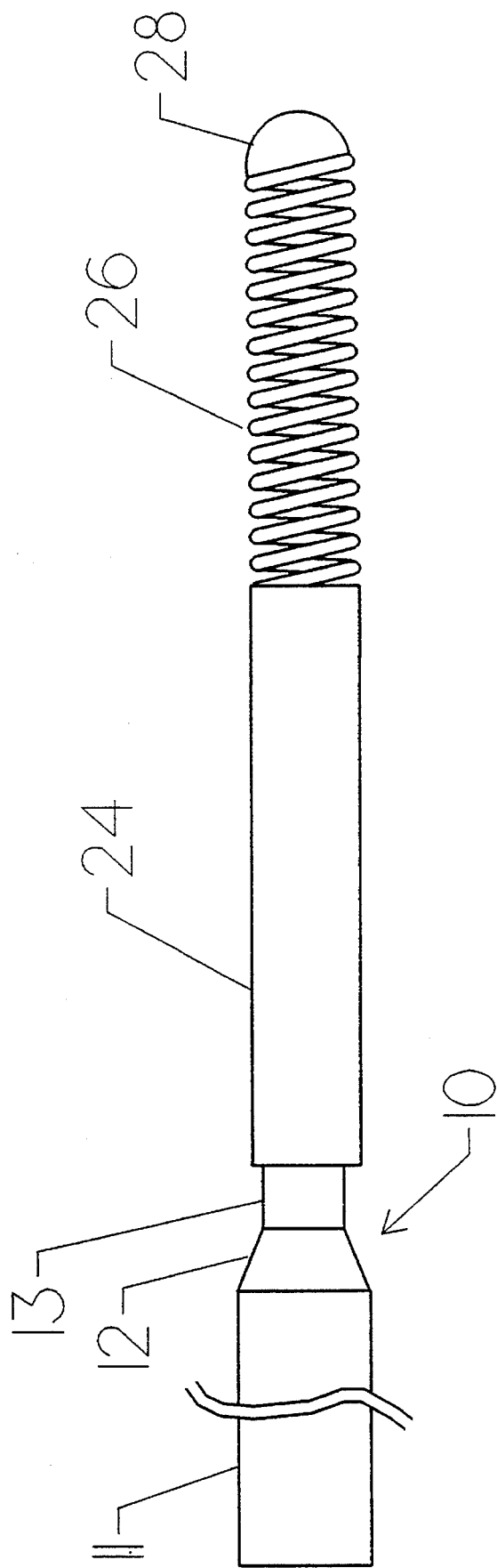
FIG. 2 is a plan view showing the distal end of the prior art guide wire of FIG. 1 covered by a helical coil and a polymer sleeve.

FIG. 2 is a drawing of guide wire 10 with a helical coil 26 and a ball tip 28 shown attached to guide wire 10 in a manner well known in the prior art. Any portion of step 18, ribbon 19 and connection member 20 which may show through the coils of coil 26 have been omitted from FIG. 2 for purposes of clarity, though it is understood that some or all of these elements are covered by coil 26; the same deliberate omission will be made in all of the Figs. of the drawings for the same purpose. FIG. 2 also shows a polymer sleeve 24 used in the preferred embodiment of this invention in a manner well known in the prior art to cover a portion of the distal segment of guide wire 10 and aid in the steerage of wire 10 through a body lumen.

Figure 3:
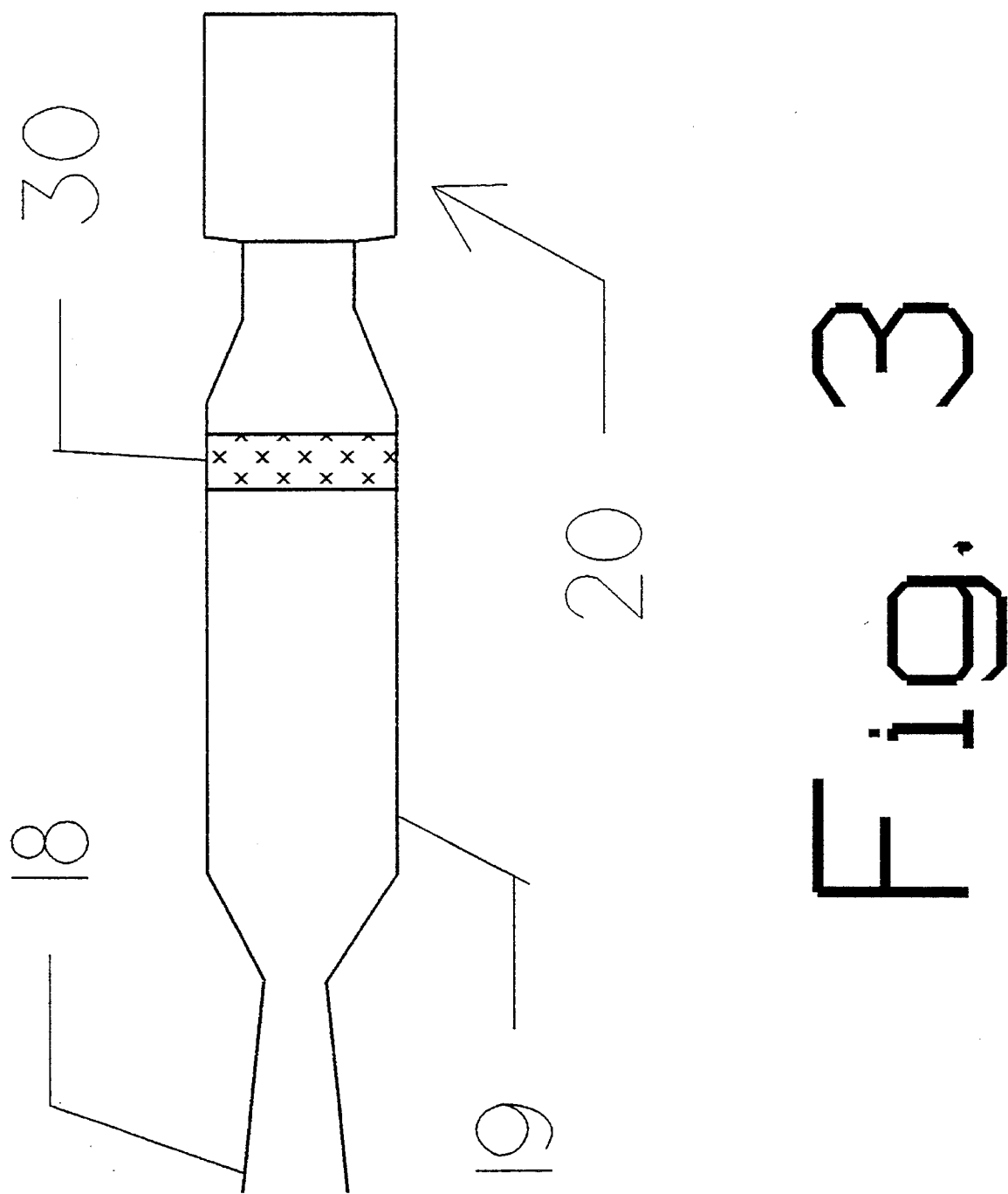
FIG. 3 is a view of a distal end or tip of a guide wire incorporating the invention and depicting a single region that has been heat treated for bending.

FIG. 3 depicts distal tip section or ribbon 19 after a single sector, region or band 30 has been heat treated in accordance with the teachings of this invention. Region 30 may not be visible to the eye and is therefore shown here as a hatched band so that the reader may best understand the invention.

As described above, prior art catheter guide wires often had a metal ribbon at the distal end of the guide wires and typically used the ribbon to introduce or form a J-tip configuration. It is generally known that the force used to form or bend a non heat-treated ribbon could result in undesirable inconsistencies and irregularities. Heat treating the entire ribbon, e.g. to about 1400° F. for the stainless steel 304V used in the preferred embodiment of this invention, can result in adding too much formability to the distal tip section of the prior art guide wire thus decreasing its steerability through a lumen by reducing resiliency and tip strength. Similarly, the presently known practice of heating the distal section to a temperature of about 950° F. and then cold stamping the ribbon has been found to result in a guide wire tip with less than optimum performance.

In the improved guide wire 10 of this invention as shown in FIG. 3, only a comparatively narrow region or band 30 on previously formed ribbon 19 is heat treated. The area of band 30 in ribbon 19 is significantly less than the total area of ribbon 19. The resulting improved distal section can be easily bent or formed into the desired J-tip, by the manufacturer or by the physician at the time of use, by bending the ribbon 19 at the area of band 30. Yet, unlike the prior art, the forming does not significantly affect the resiliency or flexibility of the remainder of ribbon 19 and improved guide wire steerability is achieved.

In the preferred embodiment, the region 30 is created by heat treating only the region 30 to a temperature above about 850° F. but less than 1400° F., and more preferably to a temperature of 950° F. This heat treatment could be accomplished by subjecting the region 30 to a laser for only a few seconds or to a fiber optic light system for approximately 30 seconds. Those skilled in the art would recognize that conventional inductive or convective methods applied over several minutes could be used, however, these methods would be less accurate than the previously-mentioned methods.

Figure 4:
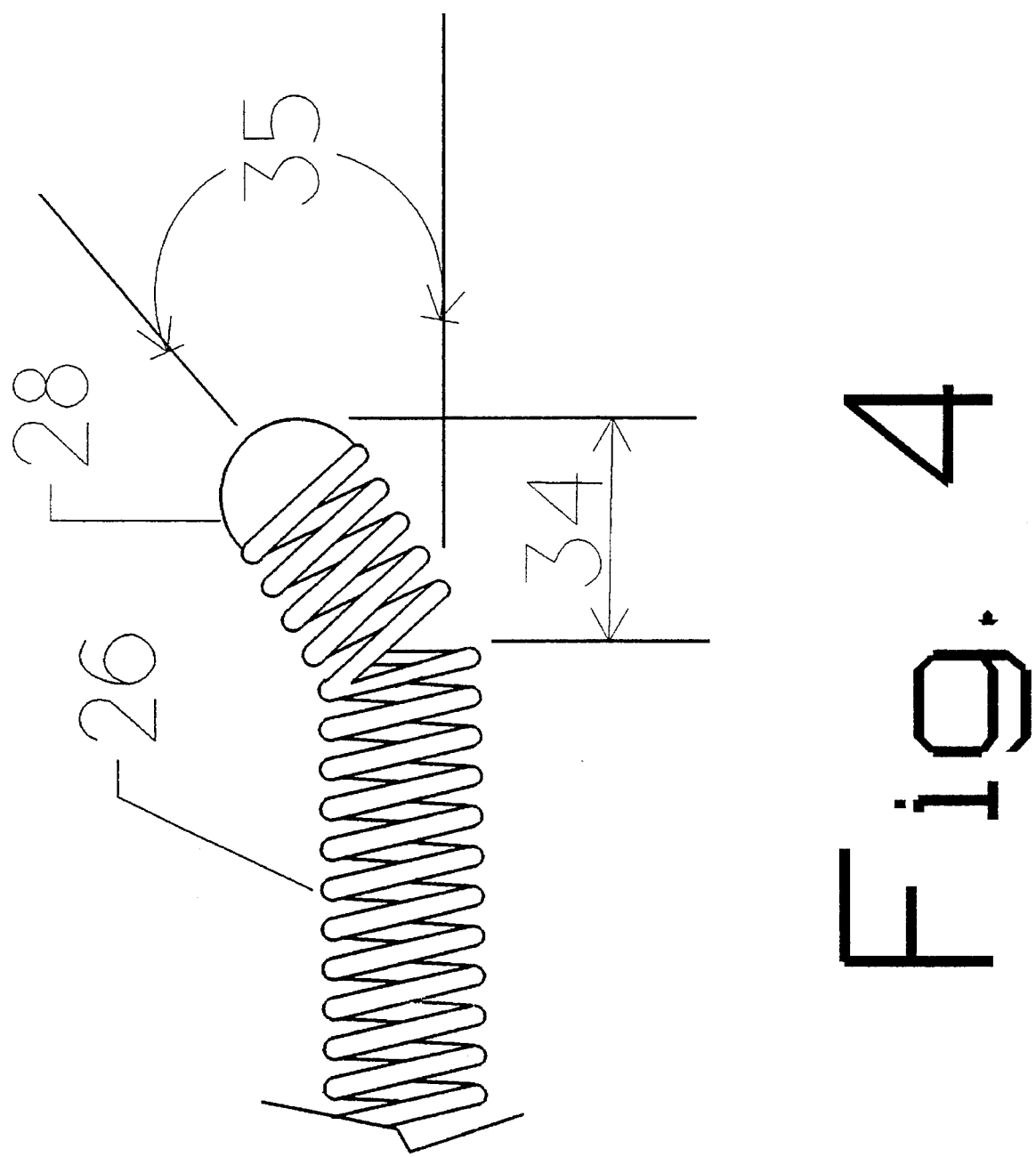
FIG. 4 is a view of a helical coil positioned as if attached to the distal end of the guide wire in FIG. 3 after bending.

FIG. 4 depicts the general shape of coil 26 after a bend has been made in ribbon 19 of FIG. 3 at region 30. Angle 35 may be altered by the physician to suit the needs of the particular case at hand, and similarly the manufacturer may selectively use more than one set of angles 35. Further, length 34 is also a variable that is set by the location of heat treated band 30 in ribbon 19. Therefore, by varying the location of band 30, multiple lengths 34 and angles 35 can be obtained.

Figure 5:
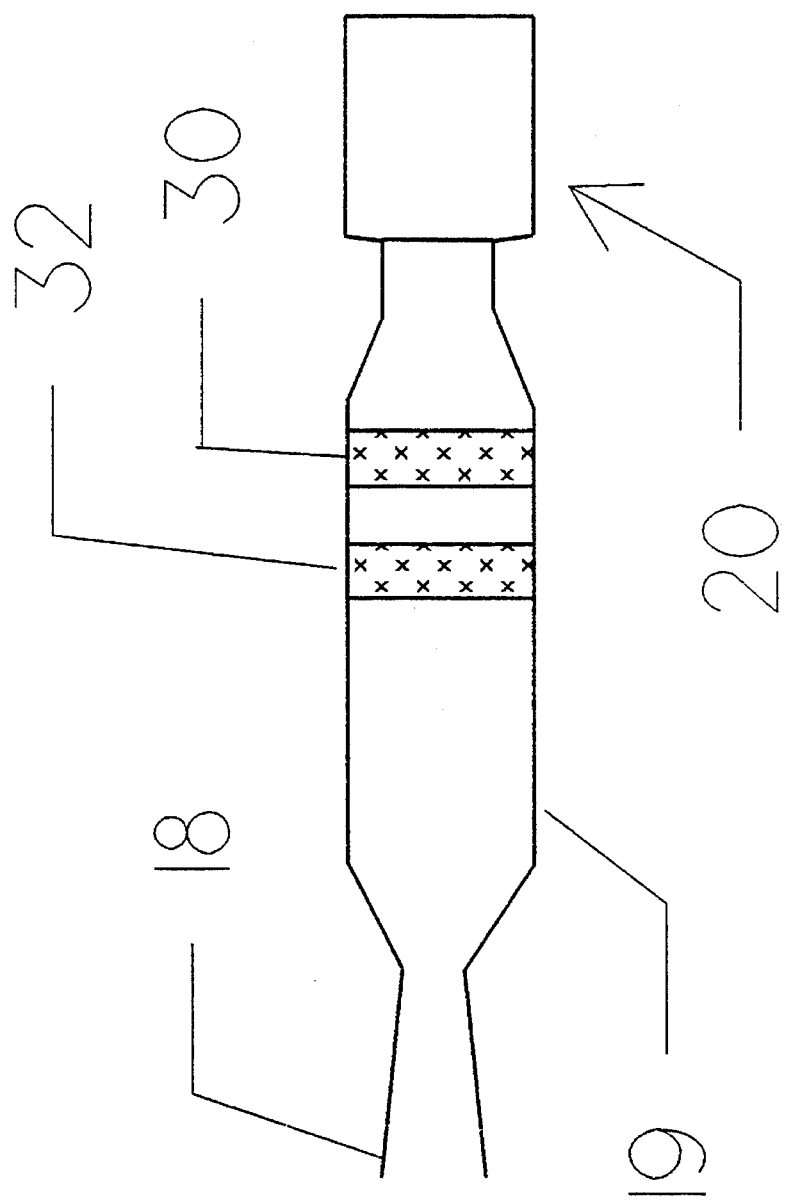
FIG. 5 is a view of a distal end or tip of a guide wire incorporating the invention and depicting a plurality of regions that have been heat treated for bending.

FIG. 5 depicts another preferred embodiment of this invention in which ribbon 19 carries a plurality of heat treated regions or bands here shown as 30 and 31. Reference to FIG. 6 depicts, by way of example, a resulting J-tip formation that can be achieved with the embodiment of FIG. 5 utilizing more than a single heat treated sector on ribbon 19. Here there are shown dual bends in coil 26 the angles of each being separately selectable by the physician or manufacturer as described in the discussion of FIG. 4 above. Lengths 34 and 36 are again dependent on the location of bands 30 and 31 in ribbon 19 and may be selected as desired for a particular guide wire 10. In the alternative, the physician could choose to form a single band similar to FIG. 4 by bending the wire at band 30 or band 31. In this embodiment, the physician is provided with a guide wire having a formable tip with multiple lengths 34.

Referring again to FIG. 5, it will be recognized that additional regions of heat treatment, such as 30 and 31, may be added as desired should a more complex J-tip configuration be desired. It is preferred that the total lengths, and thus the total area, of heat treated bands such as 30 and 31 be selected such that the total area of treated portions of ribbon 19 be less than the total area of ribbon 19. This will prevent the heat treatment from interfering with the resilience and flexibility of the distal tip section, shown as ribbon 19, of guide wire 10.

Having thus described the preferred embodiments of the present invention, those of skill in the art will readily appreciate the other useful embodiments within the scope of the attached claims.

I claim:

1. A guide wire apparatus comprising:
   a. a length of flexible metal wire with proximal and distal ends;
   b. a distal tip section at the distal end of the flexible metal wire; and
   c. a heat-treated region on the distal tip section which has been heat treated to a temperature above about 850° but less than 1400° F., for providing an easily formable portion of the distal tip section, said heat treated region having an area substantially less than the area of the distal tip section.

2. A guide wire apparatus according to claim 1 further comprising a plurality of distinct heat-treated regions on the distal tip section for providing a plurality of easily formable portions of the distal tip section.

3. A guide wire apparatus according to claim 2 wherein the total area of the plurality of heat-treated regions is less than the area of the distal tip section.

4. A method of making a metal catheter guide wire with a formable tip comprising the steps of:
   a. providing a flexible wire having proximal and distal ends and a metal portion at the distal end;
   b. heat-treating a discrete region of the metal portion to a temperature above about 850° but less than 1400° F. to increase the ease of formability of the discrete region; and
   c. attaching a coil to the distal end of the metal wire.

5. A method of making a metal catheter guide wire according to claim 4 wherein the heat treating step comprises heating a plurality of discrete regions of the metal portion.

6. A formable catheter guide wire apparatus comprising:
   a. a length of flexible metal wire having proximal and distal ends;
   b. a flexible coil attached to the wire such that at least a portion of the distal end is covered by the coil; and
   c. a heat-treated region in the distal end of the wire, which has been heat treated to a temperature above about 850° but less than 1400° F., that is covered by the coil.

7. A guide wire apparatus according to claim 6 further comprising a plurality of separate heat-treated regions in the distal end of the wire that are covered by the coil.

8. A guide wire apparatus according to claim 6 wherein the heat-treated region has a length less than the length of the distal end.

9. A guide wire apparatus according to claim 7 wherein the plurality of heat-treated regions have a total length less than the length of the distal end.

\* \* \* \* \*